United States Patent [19]

Kihlberg et al.

[11] Patent Number: 5,462,924
[45] Date of Patent: Oct. 31, 1995

[54] PRODUCT CONTAINING GROWTH FACTOR AND GLUTAMINE AND USE OF GROWTH FACTOR FOR THE TREATMENT OF INTESTINAL MUCOSA

[75] Inventors: Reinhold Kihlberg, Österskär; Svante B. Lindgren, Märsta; Lars G. Sandberg, Rimbo, all of Sweden

[73] Assignee: Pharmacia Aktiebolag, Sweden

[21] Appl. No.: 975,558

[22] PCT Filed: Aug. 22, 1991

[86] PCT No.: PCT/SE91/00558

§ 371 Date: Feb. 23, 1993

§ 102(e) Date: Feb. 23, 1993

[87] PCT Pub. No.: WO92/03155

PCT Pub. Date: Mar. 5, 1992

[30] Foreign Application Priority Data

Aug. 24, 1990 [SE] Sweden ............................ 9002732

[51] Int. Cl.⁶ .................... C07K 5/00; A61K 38/00
[52] U.S. Cl. ........................................ 574/12; 514/21
[58] Field of Search ................................ 514/12, 21

[56] References Cited

U.S. PATENT DOCUMENTS 5,164,370  11/1992  Ballard et al. ................ 514/12

FOREIGN PATENT DOCUMENTS

| 0177342 | 4/1986 | European Pat. Off. . |
| 401056 | 6/1989 | European Pat. Off. . |
| WO87/04074 | of 0000 | WIPO . |
| WO87/01589 | of 0000 | WIPO . |
| WO87/03806 | of 0000 | WIPO . |
| 89/09268 | 10/1989 | WIPO . |
| 91/12018 | 8/1991 | WIPO . |
| 91/09597 | 9/1991 | WIPO . |

OTHER PUBLICATIONS

Low–dose growth hormone and hypocaloric nutrietion attenuate the protein–catabolic response after major operation, Dialog Information Services, File 155, Medline 66–91/May, Dialog Accession No. 07118481, Jiang ZM et al., Ann Surg Oct. 1989, 210 (4) pp. 513–524.

*Primary Examiner*—Jill Warden
*Assistant Examiner*—P. Lynn Touzeau
*Attorney, Agent, or Firm*—Pollock, Vande Sande & Priddy

[57] ABSTRACT

IGF-1 is administered to a patient for the treatment or prevention of atrophy of the gut mucosa.

15 Claims, No Drawings

PRODUCT CONTAINING GROWTH FACTOR AND GLUTAMINE AND USE OF GROWTH FACTOR FOR THE TREATMENT OF INTESTINAL MUCOSA

The present invention relates to a product having anabolic effects and which also can be used for the treatment or prevention of malfunction or diseases of the intestinal mucosa. The product contains a growth factor together with glutamine and a fatty acid. The invention also comprises a procedure for the prevention or treatment of impaired function of the gut wall after, for example, trauma, sepsis, burn injuries, radiation therapy or cytotoxic chemotherapy, as well as different inflammatory conditions such as ulcerative colitis or morbus Chron. Thereby can growth factors optionally together with glutamine and/or a fatty acid be given by oral, intravenous, peritoneal, rectal, intramuscular or subcutaneous administration.

BACKGROUND

In trauma and sepsis, in addition to the conspicuous injuries or signs of infection, there are also metabolic changes. These changes can be divided into an early so-called ebb phase followed later by a so-called flow phase. In the ebb phase (shock phase), which can last for 1–3 days after the incidence of the injury, there exists a reduced energy turnover, increased lipolysis, hyperglycaemia, elevated catecholamine release and hormonal maladaptation, circulatory effects with decreasing blood pressure, reduced tissue perfusion and oxygen consumption, hypoxia, acidosis, increased body weight as a result of fluid and urine retention and a reduced body temperature. Protein synthesis is also reduced as well as blood albumin and amino acid concentrations.

After about 3 days, the flow phase appears which can last for 1–4 weeks. The flow phase is characterised by an increased energy turnover, increased release of substrates, negative nitrogen balance, rise in blood pressure, increased oxygen consumption and elevation of body temperature. Protein synthesis is reduced in mild trauma whilst both synthesis and breakdown increase in major trauma. Breakdown dominates resulting in a negative nitrogen balance which can reach 0.3–0.6 g nitrogen per kg body weight and day. This is equivalent to approximately 1.2–2.4 kg muscle wastage per day in a normal individual.

If the catabolic component of the flow phase continues for too long, a life threatening situation can develop with substantial losses of fat and muscle tissue as well as impaired wound healing and defence against infection (Ljusk S Eriksson, Mossberg T, Wahren J; pp 99–117, Klin Nutr Almq & Wiks 1987).

The concentration of glycogenic amino acids (such as alanine, glycine, serine and glutamic acid) drops in the plasma whilst a simultaneous increase in the plasma levels of branched chain amino acids (such as leucine, isoleucine and valine), aromatic amino acids (such as phenylalanine, tyrosine and tryptophan) as well as methionine, is observed. An approximately 50% reduction of the intracellular glutamine concentration is also typical. The above mentioned changes can partly be explained as disturbances in transport over the cell membrane. Alanine and glutamine are taken up and metabolised by the gut mucosa and the liver. In the liver they are utilised for, amongst other things, gluconeogenesis. In burn patients the splanchnic (liver and gut) uptake of amino acids is increased approximately 2–6-fold compared to a healthy control. The protein catabolism, which is evident mainly as increased urea production, not only affects striated muscles and visceral proteins but also smooth muscles such as those found in the gut wall and in the respiratory pathways. This situation can negatively affect vital bodily functions as well as secretory transport in the bronchii, with secretory stagnation and development of pneumonia, a common post-traumatic complication.

The gut mucosa is important not only for the selective and active absorption of different nutrients, but also as a barrier against foreign organisms and toxins. In recent years, it has been shown that the barrier function of the gut mucosa deteriorates in association with major trauma and sepsis. Furthermore, both cytotoxic chemotherapy and radiation therapy have a deleterious effect on gut mucosal function. Intravenous nutritional therapy, which is applied when the patient has difficulties to eat or assimilate orally administered food, has been shown to contribute to atrophy of the gut mucosa. Gut atrophy appears in laboratory animals and in man after intravenous feeding. This can increase the risk for translocation of bacteria over the gut mucosa with consequent risk for sepsis and increased mortality.

Atrophy of the gut combined with simultaneous translocation of bacteria over the gut mucosa is most likely in patients who have suffered major trauma and extensive clinical intervention, in sepsis, in major burn injuries and even after radiation therapy and/or cytotoxic chemotherapy in patients with abdominal or urogenital tumours. Patients with inflammatory diseases of the gut such as ulcerative colitis and morbus Chron also run the risk of being stricken by life threatening infections caused by atrophy of the villi and consequent development of ileus with toxic dilatation and release of bacteria into the peritoneum.

The observation of a marked decline in the intracellular concentration of glutamine in muscle following trauma and sepsis initiated interest in glutamine metabolism and its significance. It has been shown that glutamine is an important energy substrate in intestinal tissue and that glutamine utilization increases in the catabolic state. In studies on experimental animals it has been demonstrated that glutamine administration can prevent a fall in plasma and muscle glutamine concentrations following trauma. Further, an accelerated mucosa recovery after injury induced by 5-fluorouracil was observed in rats when glutamine was added to the intravenous nutrition solutions ('Dwyer ST et al, Clin Res 367a, 1987).

During an international symposium "Glutamine metabolism in health and disease", Jan. 26–27, 1990, in San Antonio, Tex., USA, it was reported that in human subjects, post-operative glutamine supplementation of a total parenteral nutritional regimen improved nitrogen balance and counteracted the decline in protein synthesis usually seen post-operatively. Further it was reported that a number of positive effects had been observed in patients undergoing bone marrow transplantation who were given considerable amounts of glutamine.

In a patent for the treatment of catabolic dysfunction in an animal, a composition including 5–30 g of L-glutamine and/or 5–25 g of alpha-keto glutaric acid is claimed (WO 87/01589). Another patent comprises aqueous solutions for parenteral nutrition which preferentially contain glutamine together with other organic nitrogen-containing compounds (WO 87/03806). Furthermore, the presentation of glutamine in the form of dipeptides has been patented (see EP 87750 and DE 3108079).

The gut has an active endogenous microflora of which the majority of the organisms are facultative of obligatory anaerobes. This means that the major products of fermentation are the short-chain fatty acids (SCFA), mainly acetic acid, propionic acid and butyric acid. The substrates for this fermentation are the carbohydrates that reach the large intestine.

In so-called germ-free rats there is an atrophy of the gut mucosa. These rats also have a low endogenous production of SCFA which represents only about 1% of the production seen in normal rats (Hoverstedt and Midtvendt, J. Nutr. 116, 1772–76, 1986).

A fiber-free diet (one week) or total parenteral nutrition (two weeks) reduces the fecal loss of SCFA in man by 50% and 80%, respectively (Hoverstedt, Symposium, held at The Wennergren-Gren Center, Stockholm, Sweden, Jun. 1th–4th, 1988).

Some experiments with SCFA-enriched nutritional solutions have been described in the literature. In all cases but one the experiments were carried out in animals that had been subjected to small bowel resection and given intracolonal or intracaecal infusions.

In a study of Koruda et al. (Am. J. Clin. Nutr. 51,685–9, 1990) SCFA-enriched total parenteral nutrition was employed, but since there was no fat in the regimen, the diet was not balanced (lacking essential fatty acids). Furthermore, a mixture of SCFA (acetate, propionate and butyrate) was used in which acetate and propionate were in higher concentration than butyrate. These shorter acids have been shown to be more toxic than butyrate.

It has been suggested (WO 87/04074) that protein accretion or nitrogen retention can be promoted in the case of a hypocaloric diet by the administration of growth hormone. In a study with intravenously fed rats, an increase in mucosal protein was observed in the small bowel and in the colon following the simultaneous administration of L-glutamine and epidermal growth factor (Jacobs D. O. et al. Surgery 104 (2), 358–364 (1988)). IGF-I has been shown by O'Sullivan et al. (Endocrinology 125: 2793–95 81989) to prevent weight loss in starved mice, whereas GH (bovine) was ineffective in this situation. A relative increase in kidney and spleen weights has been reported for GH and IGF-1 treated rats ( Skottner A. et al. Endocrinology 124, 2519 (1989).

It is quite clear, however, that several of the problems mentioned above have until now not been solved with existing nutritional therapy.

At present there is no clinical application of a growth factor alone or together with glutamine and/or a short- or medium-chain fatty acid for the improvement of gut function or for the combination having anabolic effects.

DESCRIPTION OF THE INVENTION

The present invention relates to a product containing glutamine or a derivative or analogue thereof, a short- or medium-chain fatty acid and a growth factor or analogue thereof for simultaneous, separate or sequential use having anabolic effects and/or for treatment or prevention of malfunction or disease of the intestinal mucosa as well as the use of these components for the manufacture of a medicament or a kit for the treatment or prevention of malfunction or disease of the intestinal mucosa.

The invention also discloses a method for the treatment or the prevention of malfunction or disease of the intestinal mucosa characterised in that a pharmacologically effective dose of a growth factor or analogue thereof is administered to a patient optionally simultaneously, separately or sequential with either or both of glutamine or a derivative or analogue thereof and/or a short- or medium-chain fatty acid.

The components should be in a pharmaceutically acceptable form. By product is meant here not only a product or kit containing these three components, but also when the components are admixed with other components in a TPN, such as amino acids, carbohydrates and fat, preferably as an emulsion.

The components can also be administered separately, e.g. a short -or medium- chain fatty acid, glutamine and the growth factor in an aqueous medium. The fatty acid and glutamine can both be mixed with the nutritient and the growth factor administered separately. Glutamine can be administered e.g. as the L-amino acid, as N-acetyl-L-glutamine or as a glutamine-containing peptide.

By short-or medium-chain fatty acids are meant here saturated fatty acids of C2–C12 carbon chain length, preferably short chain of 2–4 carbons, such as butyric acid which is preferably administered intravenously.

The short- or medium-chain fatty acids can be administered as, for example, sodium or potassium salts and a medium fatty acid can be administrated as a triglyceride.

Growth factors include here especially growth hormone (GH), Insulin-like growth factors IGF-1 and IGF-2, GRF (growth hormone releasing factor) or analogue thereof etc. By analogue is meant substances which have the same physiological effect as the Growth factors, mainly I GF-1, can be injected or can be administered intravenously either as an aqueous solution or incorporated into a fat emulsion or as a component in micelles or liposomes.

The amount of the components given to humans could be varied depending on the patient and disease. Normally they are within the doses normally given, such as 0.01–1 g/kg, day for glutamine, preferably 0,2–0,7 g/kg, day and 0,005–0, 3 g/kg per day for fatty acid, preferably 0,02–0,15 g/kg per day. The amount of IGF-1 could be 0.02–20 mg/kg per day and preferably 0.05–2 mg/kg per day, and for GH up to 1 IU/kg per day, preferably 0.05–0.7 IU/kg per day. (4 IU GH is equal to 1.3 mg GH).

As can be seen from the background and description of the problem, the function of the gut mucosa can be of critical importance in the outcome of different illnesses. In a series of experiments, mainly in the rat, we have studied the effect on the gut mucosa of intravenous administration of commercially available solutions (for example, amino acid solutions, glucose solutions and fat emulsions) both with and without supplementation with glutamine, short-chain or medium-chain fatty acids and growth factors.

The measured variables have been primarily growth, gut mucosa morphology, villus height, crypt depth and cell proliferation in the gut mucosa measured with a radiolabelled thymidine incorporation technique.

In the above mentioned studies we observed a pronounced atrophy of the gut mucosa after total parenteral nutrition. As expected we noted a 30% reduction in the villus height and crypt depth compared to an orally fed control group. Addition of glutamine improved the gut mucosa; villus height and crypt depth increased by about 20 % and a similar improvement was seen after the administration of either a short-chain fatty acid (mainly butyric acid) or IGF-1.

When glutamine, butyric acid and IGF-1 were administered together, an unexpected synergistic effect was observed on both growth and the gut mucosa. Growth rate was three-fold higher than that of rats infused with fat, amino acids and glucose, which was totally unexpected and an anabolic effect was thus clearly shown. Moreover, for the first time we could reach a villus height in the TPN-fed rat which approached 400 µm (compared to slightly over 300 µm after non-supplemented infusion). This finding was confirmed by the results of the mucosal cell proliferation studies.

EXAMPLE 1

Male Sprague Dawley rats (180–190 g body weight, BW) were surgically fitted with a permanent central catheter which was protected by a harness. Total parenteral nutrition was given to the rats in the form of a standard regimen:

| | |
|---|---|
| Fat | 7.6 g/kg BW and day |
| Nitrogen | 1.35 g/kg BW and day |
| Total energy intake | 270 kcal/kg BW and day |
| Total volume intake | 300 ml/kg BW and day |

The ratio between glucose and fat in this experiment was 30/70 expressed as a % of the non-protein energy intake. The TPN (total parenteral nutrition) mixtures were obtained by mixing Vamin® 14 EF (a solution of essential and non-essential amino acids for parenteral nutrition), a 50% glucose solution and Intralipid® 20% in relevant proportions after which was followed by addition of the necessary amounts of electrolytes, trace elements and vitamins required by the rat.

On the morning of the first experimental day the rats were randomised into three groups: oral controls, intravenous controls and the glutamine group. The oral control rats received a standard diet (R3, Ewos AB, Södertälje, Sweden) ad libitum during the experimental period and the intravenous control rats received the above-described standard TPN regimen.

The glutamine group received glutamine in the form of the dipeptide glycyl-glutamine (which was administered intravenously in isonitrogenous and isocaloric amounts at the expense of the amino acid solution) as well as the other nutrients supplied according to the regimen given to the intravenous control group.

The infusions were given for 7 days and growth was recorded daily. The total weight gain was 41.4±4.2, 14.9±3.2 and 8.6±3.5 for the oral controls, intravenous controls and glutamine groups, respectively.

After 3 hours' fasting, blood samples were taken under pentobarbital anaesthesia for analysis of the clinical chemistry. The results are shown in Table 1.

TABLE 1

Clinical chemistry analyses in the serum.

| Group | ASAT | ALAT | ALP | LD | Bilirub | Chol | betaHB |
|---|---|---|---|---|---|---|---|
| Oral control | 1.4 | 0.87 | 8.2 | 3.6 | 0.7 | 2.0 | 1.3 |
| iv. control | 1.3 | 0.37 | 4.4 | 5.8 | 1.7 | 2.8 | 1.1 |
| Glutamine | 1.3 | 0.44 | 5.0 | 3.5 | 1.6 | 2.5 | 1.1 |

Abbreviations: ASAT=aspartate aminotransferase(microkat/l); ALAT=alanine aminotransferase (microkat/l); ALP=alkaline phosphatase microkat/l); LD=lactate dehydrogenase (microkat/l):; Bilirub=Bilirubin (micromol/l); Chol=cholesterol (mmol/l); β-HB=β-hydroxy butyrate (mmol/l).

The rats were sacrificed by exsanguination after heart puncture under pentobarbital anaesthesia after which obduction and macroscopic examination was performed. After sacrifice the liver, spleen, lungs, kidneys, heart and thymus were dissected out and weighed. The relative organ weights showed no differences of biological relevance between the groups. Similarly, there were no marked differences in the blood chemistry.

Sections of the gut were fixed in a Milla-Pott fixation medium and were evaluated with respect to villus height and crypt depth (Table 2).

TABLE 2

Morphometrical evaluation of the jejunum.

| | jejunum | |
|---|---|---|
| Group | crypt depth (µm) | villus height (µm) |
| Oral control | 165 | 460 |
| iv. control | 121 | 309 |
| Glutamine | 145 | 378 |

The morphometric analysis of the jejunum demonstrates an atrophy of the gut after parenteral nutrition of the rats for 7, days. This condition could be markedly improved by the administration of glycyl-glutamine.

In summary, the results show that intravenous administration of glutamine for 7 days was well tolerated and that a significant improvement of gut morphology, with approximately a 20% increase in both villus height and crypt depth.

EXAMPLE 2

In an experiment performed similar to example 1, the effect of butyric acid on body weight, relative organ weight, blood chemistry, serum and urine β-hydroxy butyric acid levels as well as morphometrical evaluation of the jejunum was studied in rats. TPN was given to the rats in the form of the standard regimen described in example 1 and butyric acid was given intravenously as Na-salt.

Infusions were given for 7 days and the growth of the animals was studied during the entire experimental period (Table 3).

TABLE 3

Growth after 7 days of TPN in the rat

| Group | Weight increase (g) |
|---|---|
| iv. control | 14.9 ± 3.2 |
| Butyric acid | 15.5 ± 2.5 |

Blood sampling, sacrifice and dissection were performed as described in example 1.

Total weight increase was not significantly different. There were also no differences in the relative organ weights between the groups. Similarly, there were no differences in the blood chemistry.

Morphometric analysis of the jejunum and ileum demonstrated an atrophy of the gut after 7 days of parenteral nutrition in the rat. This condition was improved by the administration of 3 g butyric acid per kg body weight and day (table 4).

TABLE 4

Morphometric evaluation of the jejunum after 7 days of TPN in the rat.

| Group | crypt depth (μm) | villus height (μm) |
| --- | --- | --- |
| iv. control | 121 | 309 |
| Butyric acid | 150 | 361 |

In summary, the results show that 7 days of TPN containing 3 g/kg butyric acid was well tolerated and that an improvement of gut morphology as a consequence of butyric acid could be seen.

EXAMPLE 3

The effect of the simultaneous administration of glutamine, butyric acid and IGF-1 was studied in the rat. The experimental design as well as the parameters under study were identical to those described in examples 1 and 2. Besides a morphometric evaluation of the small intestine, a cytokinetic study using methyl-3-H thymidine was performed on the jejunum. The test group received parenteral fat, amino acids, glucose, butyric acid and glutamine. Further, the rats received IGF-1 in the form of subcutaneous injections of 1 mg/day divided into two doses each day. This was repeated for 8 days. At the same time an intravenous control group of TPN rats was studied.

The experiment was terminated by anaesthetising the rats with pentobarbital and infusing them with radiolabelled methyl-3-H-thymidine (1 μC/kg). The rats were sacrificed by cervical dislocation and samples were taken from the jejunum for mophometric and cytokinetic analyses. See Table 5. Blood samples were taken for IGF-1 determination.

TABLE 5

Weight gain and morphometric evaluation of the jejunum after 7 days of TPN in the rat.

| Group | Weight gain | jejunum | |
| --- | --- | --- | --- |
| | | crypt depth (μm) | villus height (μm) |
| iv. control | 8.8 ± 1.8 | 121 | 309 |
| combination therapy | 27.1 ± 4.6 | 144 | 395 |

In summary, after the simultaneous administration of a short-chain fatty acid, glutamine and a growth factor IGF1, a surprising and significant synergistic effect was observed both on growth and on the gut mucosa.

The effect on weight increase when the three components were given together was surprisingly high when compared to the weight increase for a component given alone (Example 1 and 2). Thus an anabolic effect was obtained.

The effect on the gut mucosa was also clear and could even be seen at dissection. The results of the cytokinetic studies confirm these observations.

Thus, our studies show a surpringsingly good effect on the gut mucosa when the three components were administered simultaneously, as compared to any of the components given alone.

What is claimed is:

1. Method for the treatment of atrophy of the gut mucosa after intravenous nutrition, which comprises injecting a patient in need thereof with a pharmacologically effective dose of IGF-1.

2. The method of claim 1 wherein said dose is 0.02–20 mg/kg/day.

3. The method of claim 1 wherein said dose is 0.05–2 mg/kg/day.

4. The method of claim 3 wherein a mixture of glutamine, butyric acid and IGF-1 is injected.

5. The method of claim 1 which comprises improving the villus height of the gut.

6. The method of claim 1 which comprises improving the crypt depth of the gut mucosa.

7. The method of claim 1 which comprises improving the growth of the gut mucosa.

8. The method of claim 1 wherein said injecting is intravenously.

9. Method for the treatment of atrophy of the gut mucosa characterized in that a pharmacologically effective dose of IGF-1 thereof is injected into a patient simultaneously, separately or sequentially with either or both of:

a) at least one member selected from the group consisting of glutamine, N-acetyl-L-glutamine and glutamine-containing peptide;

b) short-or-medium chain fatty acid containing 2–12 carbon atoms.

10. The method of claim 9 wherein the amount of said glutamine is sufficient to provide a dose of 0.01–1 g/kg/day, the amount of said butyric acid is sufficient to provide a dose of 0.005–03 g/kg/day, and the amount of IGF-1 is sufficient to provide a dose of 0.02–20 mg/kg/day.

11. The method of claim 9 wherein the amount of said glutamine is sufficient to provide a dose of 0.2–0.7 g/kg/day, the amount of said butyric acid is sufficient to provide a dose of 0.02–0.15 g/kg/day, and the amount of said IGF-1 is sufficient to provide a dose of 0.05–2 mg/kg/day.

12. The method of claim 9 wherein said injecting is intravenously.

13. The method of claim 9 which comprises improving the villus height of the gut.

14. The method of claim 9 which comprises improving the crypt depth of the gut mucosa.

15. The method of claim 9 which comprises improving the growth of the gut mucosa.

* * * * *